«12» United States Patent
Shimada et al.

(10) Patent No.: US 7,989,184 B2
(45) Date of Patent: Aug. 2, 2011

(54) ENDORIBONUCLEASE

(75) Inventors: Masamitsu Shimada, Otsu (JP);
Masanori Takayama, Otsu (JP); Kiyozo Asada, Otsu (JP); Ikunoshin Kato, Otsu (JP)

(73) Assignee: Takara Bio Inc., Otsu-shi, Shiga (JP)

( * ) Notice: Subject to any disclaimer, the term of this patent is extended or adjusted under 35 U.S.C. 154(b) by 757 days.

(21) Appl. No.: 11/997,071

(22) PCT Filed: Jul. 4, 2006

(86) PCT No.: PCT/JP2006/313271
§ 371 (c)(1),
(2), (4) Date: Jan. 28, 2008

(87) PCT Pub. No.: WO2007/013264
PCT Pub. Date: Feb. 1, 2007

(65) Prior Publication Data
US 2010/0330616 A1 Dec. 30, 2010

(30) Foreign Application Priority Data
Jul. 26, 2005 (JP) .................................. 2005-215678

(51) Int. Cl.
*C12P 19/34* (2006.01)
(52) U.S. Cl. .................... 435/91.1; 435/91.53; 435/91.3
(58) Field of Classification Search .................. None
See application file for complete search history.

(56) References Cited

FOREIGN PATENT DOCUMENTS
WO 2004/113498 A2 12/2004
WO 2005/074986 A2 8/2005
WO 2007/013264 2/2007

OTHER PUBLICATIONS

Database EMBL Jun. 1, 2003, "PemK-like protein" XP002505795, retrieved from EBI, Database accession No. Q82VB5.
Gerdes Kenn et al., "Prokaryotic toxin-antitoxin stress response loci" Nature Reviews. Microbiology, Nature Publishing Group, GB, vol. 3, No. 5, May 1, 2005, pp. 371-382, XP009106994, ISSN: 1740-1526.
European Search report dated Dec. 12, 2008, in connection with corresponding EP application No. 06767902.9.
Chinese Office issued Mar. 11, 2010, in corresponding Chinese Patent Appln. No. 200680027231.5.
Database DDBJ/EMBL/GenBank (online), "Nitrosomonas europaea ATCC 19718, complete genome"; Accession No. NC_004757.1; GI:30248031 (2010).
Database DDBJ/EMBL/GenBank (online), "Nitrosomonas europaea ATCC 19718, complete genome"; Accession No. NC_004757.1; GI:30248031 (2003).
Chain et al Database DDBJ/EMBL/GenBank (online), 2003. Accession No. NP_841237.
Zhang et al "Interference of mRNA Function by Sequence-specific Endoribonuclease PemK," Boil. Chem., 270(20): 20678-20684 (2004).
Munoz-Gomez et al "Insights into the specificity of RNA cleavage by the *Escherichia coli* MazF toxin," FEBS Letters, 567: 316-320 (2004).
Pederson, et al "The Bacterial Toxin RelE Displays Codon-Specific Cleavage of mRNAs in the Ribosomal A Site," Cell 112(1): 131-140 (2003).
Christensen, et al "Toxin-antitoxin Loci as Stress-response-elements: ChpAK/MazF and ChpBK Cleave Translated RNAs and are Counteracted by tmRNA," Mol. Biol., 332(4): 809-819 (2003).
Pandey, et al "Toxin-antitoxin loci are highly abundant in free-living but lost from host-associated prokaryotes" Nucleic Acid Res., 33(3): pp. 966-976 (2005).
Hayes "Toxins-Antitoxins: Plasmid Maintenance, Programmed Cell Death, an Cell Cycle Arrest" Science, 301 (5639): 1496-1499 (2003).
Gerdes "Toxin-Antitoxin Modules May Regulate Synthesis of Macromolecules during Nutritional Stress." Journal of Bacteriology, 182(3): 561-572 (2000).
Zhang, et al "Insights into the mRNA Cleavage Mechanism by MazF, an mRNA Interferase" Jour. Biol. Chem., 280 (6): 3143-3150 (2005).
Zhang, et al "MazF Cleaves Cellular mRNAs Specifically at ACA to Block Protein Synthesis in *Escherichia coli*," Molecular Cell, 12(4) : 913-923 (2006).
Yoshida "The Ribonuclease T1 Family" Methods in Enzymology, 341(2): 28-41 (2001).
Christensen, et al "RelE toxins from Bacteria and Archaea cleave mRNAs on translating ribosomes, which are erscued by tmRNA" Molecular Microbiology, 48(5): 1389-1400 (2003).
Christensen, et al "Overproduction of the Lon protease triggers inhibition of translation in *Escherichia coli*: involvement of the yefM-yoeB toxin-antitoxin system" Molecular Microbiology, 51(6): 1705-1717 (2004).
Mittenhuber "Occurence of MazEF-like Antitoxin/Toxin Systems in Bacteria" J. Molecular Microbiology, 1(2): 295-302 (1999).
Anantharaman, et al "New connections in the prokaryotic toxin-antitoxin network: relationship with the eukaryotic nonsense-mediated RNA decay system" Genome Biology, 4: R81.1-R81.15 (2003).
International Search Report issued in WO/2007/013264 (PCT/JP2006/313271).
International Preliminary Report on Patentability and Written Opinion issued in WO/2007/013264 (PCT/JP2006/313271).
European Patent Office, Office Action of Mar. 8, 2011, in European Patent Application No. 06 767 802.9.

*Primary Examiner* — Nashaat Nashed
(74) *Attorney, Agent, or Firm* — Browdy and Neimark, P.L.L.C.

(57) ABSTRACT

A polypeptide having a novel endoribonuclease activity; a nucleic acid encoding the polypeptide; recombinant DNA having the nucleic acid therein; a transformant transformed with the recombinant DNA; a process for producing the polypeptide comprising the steps of cultivating the transformant and collecting the polypeptide from the culture; a process for producing a digest of single-stranded RNA comprising the step of reacting the polypeptide with the single-stranded RNA; and a method for the digestion of single-stranded RNA.

7 Claims, No Drawings

ENDORIBONUCLEASE

TECHNICAL FIELD

The present invention relates to a novel sequence-specific endoribonuclease which is useful in the field of genetic engineering.

BACKGROUND ART

It has been reported that several prokaryotic plasmids have a post-segregation killing (PSK) function to kill hosts from which the plasmids have been dropped out in order to maintain the plasmids in the hosts. Such plasmids have toxin-antitoxin genes. An antitoxin binds to a toxin in a cell to inactivate the toxin. The antitoxin is labile to degradation by proteases. Degradation of the antitoxin by proteases results in activation of the toxin which is stable (Non-patent Document 1). Such toxin-antitoxin genes also exist on chromosomes of most prokaryotes. They respond to various stresses and have functions in programmed cell death. Although the functions of the toxins have not been fully proven, it has been suggested that CcdB and ParE may control replication targeting DNA gyrase, and RelE and Doc may control transcription (Non-patent Documents 1 and 2).

At least five toxins RelE, ChpAK (MazF), ChpBK, YoeB and YafQ exist in *Escherichia coli* (Non-patent Document 2). Christensen et al. have reported that RelE is an endoribonuclease that recognizes a specific codon of three nucleotides in a ribosome-dependent manner to cleave mRNA (Non-patent Documents 3 and 4). Furthermore, Christensen et al. have reported that ChpAK, ChpBK and YoeB are also endoribonucleases that cleave mRNA in a manner dependent on ribosome and codon (Non-patent Documents 5 and 6).

Inouye et al. have demonstrated that MazF (ChpAK) is an endoribonuclease that recognizes specific nucleotides ACA in a ribosome-independent manner to cleave mRNA (Non-patent Documents 7 and 8). Munoz-Gomez et al. have reported that the cleavage of RNA with mazF is specific for NAC (Non-patent Document 9). Inouye et al. have demonstrated that PemK in a plasmid R100 is an endoribonuclease that recognizes specific nucleotides UAH (H is C, A or U) to cleaves mRNA (Patent Document 1, Non-patent Document 10). As described above, it has been suggested that toxins of the RelE or PemK family may be endoribonucleases that cleave mRNA in a nucleotide-specific manner. In particular, toxins of the PemK family may be endoribonucleases that recognize specific nucleotides in a ribosome-independent manner to cleave mRNA. Many toxins of the PemK family exist in prokaryotes and comparison of their sequences has been studied extensively (Non-patent Documents 1 and 11).

Anantharaman et al. have phylogenetically classified toxins by conducting gene neighborhood analyses on the basis of genetic information about toxins and genetic information about organisms for which genomic analyses have been completed, and predicted toxin-like proteins from proteins of unknown functions (Non-patent Document 12). Furthermore, it has been suggested through the analyses that not only RelE and PemK but also proteins of the Doc family and proteins having PIN domains may have ribonuclease activities. Five toxins of the PemK family have been found in *Nitrosomonas europaea* (Non-patent Document 13).

As to enzymes that cleave nucleic acids in a sequence-specific manner, many restriction enzymes which cleave double-stranded DNA have been found and widely utilized in the field of genetic engineering. As to enzymes that cleave single-stranded RNA in a sequence-specific manner, ribonuclease T1 which specifically cleaves at a G nucleotide has been found and utilized for genetic engineering (Non-patent Document 14). The number of enzymes that recognize plural nucleotides in single-stranded RNA and specifically cleave it is still small. Development of such endoribonucleases has been desired in the field of genetic engineering. If an endoribonuclease that specifically recognizes and cleaves a sequence of three nucleotides (like MazF) or more than three nucleotides is found, it is considered that the endoribonuclease would become a useful enzyme in the field of genetic engineering.

Patent Document 1: WO 2004/113498
Non-patent Document 1: J. Bacteriol., 182:561-572 (2000)
Non-patent Document 2: Science, 301:1496-1499 (2003)
Non-patent Document 3: Molecular Microbiol., 48:1389-1400 (2003)
Non-patent Document 4: Cell, 122:131-140 (2003)
Non-patent Document 5: J. Mol. Biol., 332:809-819 (2003)
Non-patent Document 6: Molecular Microbiol., 51:1705-1717 (2004)
Non-patent Document 7: Molecular Cell, 12:913-920 (2003)
Non-patent Document 8: J. Biol, Chem., 280:3143-3150 (2005)
Non-patent Document 9: FEBS Letters, 567:316-320 (2004)
Non-patent Document 10: J. Biol. Chem., 279:20678-20684 (2004)
Non-patent Document 11: J. Mol. Microbial. Biotechnol., 1:295-302 (1999)
Non-patent Document 12: Genome Biology, 4:R81 (2003)
Non-patent Document 13: Nucleic Acids Research, 33:966-976 (2005)
Non-patent Document 14: Methods in Enzymology, 341:28-41 (2001)

DISCLOSURE OF INVENTION

Problems to be Solved by the Invention

The present invention has been made in view of the above-mentioned prior art. The main object of the present invention is to find a novel sequence-specific endoribonuclease, to identify the cleavage sequence specificity of the novel sequence-specific endoribonuclease, and to provide its use for genetic engineering.

Means to Solve the Problems

The present inventors have screened for a sequence-specific endoribonuclease and found that a polypeptide encoded by the gene for NE1181 in *Nitrosomonas europaea* is a novel sequence-specific endoribonuclease. Furthermore, the present inventors have identified the cleavage sequence specificity of the enzyme. Thus, the present invention has been completed.

The Present Invention Relates to:

[1] a polypeptide having a sequence-specific endoribonuclease activity, which is represented by the amino acid sequence of SEQ ID NO:1 or an amino acid sequence in which one or more amino acid residue(s) is(are) deleted, added, inserted or substituted in said sequence;

[2] a nucleic acid encoding the polypeptide of [1];

[3] the nucleic acid of [2], which has the nucleotide sequence of SEQ ID NO:2;

[4] a nucleic acid that is capable of hybridizing to the nucleic acid of [2] or [3] under stringent conditions and encodes a polypeptide having a sequence-specific endoribonuclease activity;

[5] a recombinant DNA containing the nucleic acid of any one of [2] to [4];

[6] a transformant transformed with the recombinant DNA of [5];

[7] a method for producing the polypeptide of [1], the method comprising culturing the transformant of [6] and collecting a polypeptide having a sequence-specific RNA cleavage activity from the culture;

[8] a method for producing a single-stranded RNA degradation product, the method comprising allowing the polypeptide of [1] to act on a single-stranded RNA; and

[9] a method for degrading a single-stranded RNA, the method comprising allowing the polypeptide of [1] to act on a single-stranded RNA.

Effects of the Invention

The present invention enables finding of a novel sequence-specific endoribonuclease, identification of the cleavage sequence specificity of the novel sequence-specific endoribonuclease, and provision of its use for genetic engineering.

BEST MODE FOR CARRYING OUT THE INVENTION

1. The Polypeptide of the Present Invention

The polypeptide of the present invention is represented by the amino acid sequence of SEQ ID NO:1 or an amino acid sequence in which one or more amino acid residue(s) is(are) deleted, added, inserted or substituted in said amino acid sequence, and exhibits a sequence-specific endoribonuclease activity.

The activity possessed by the polypeptide of the present invention is an endoribonuclease activity specific for single-stranded RNA. The activity enables hydrolysis of a phosphodiester bond 3' to a ribonucleotide in a single-stranded nucleic acid containing the ribonucleotide as a constituting nucleotide. A nucleic acid hydrolyzed with the above-mentioned activity generates the following: a 3' end having a hydroxyl group and a 5' end having a phosphate group; a 3' end having a phosphate group and a 5' end having a hydroxyl group; or a 5' end having 2',3'-cyclic phosphate and a hydroxyl group.

A nucleic acid having at least one ribonucleotide molecule may be used as a substrate for the polypeptide of the present invention. Examples thereof include, but are not limited to, RNA, RNA containing deoxyribonucleotide(s) and DNA containing ribonucleotide(s). The substrate may contain a nucleotide that is different from ones contained in normal nucleic acids (e.g., deoxyinosine, deoxyuridine or hydroxymethyldeoxyuridine) as long as it does not inhibit the action of the polypeptide of the present invention.

The polypeptide of the present invention acts specifically on a single-stranded nucleic acid. It cannot cleave double-stranded nucleic acids such as a double-stranded RNA or an RNA-DNA hybrid.

The polypeptide of the present invention has an activity of cleaving a nucleic acid in a nucleotide sequence-specific manner. Although it is not intended to limit the present invention, for example, if a single-stranded RNA molecule contains a sequence 5'-GAAU-3' or 5'-AAAU-3', a polypeptide having the amino acid sequence of SEQ ID NO:1 hydrolyzes a phosphodiester bond 5' or 3' to the second A residue in the sequence. For example, this activity can be confirmed using an oligoribonucleotide mazG18_12 (SEQ ID NO:5) as a substrate as an activity of hydrolyzing a phosphodiester bond between the 19th and 20th nucleotides and a phosphodiester bond between the 24th and 25th nucleotides in the oligoribonucleotide. The endoribonuclease activity of the polypeptide of the present invention is exhibited in the absence of ribosome. Thus, it is a ribosome-independent activity.

A single-stranded RNA-specific endoribonuclease activity of the polypeptide of the present invention can be measured, for example, using a single-stranded RNA as a substrate. Specifically, the measurement can be carried out by allowing a polypeptide to be subjected to activity measurement to act on a single-stranded RNA, which is transcribed from a DNA as a template using RNA polymerase or chemically synthesized, and determining the presence of RNA cleavage. For example, degradation of RNA can be confirmed using electrophoresis (agarose gel, acrylamide gel, etc.). Attachment of an appropriate label (e.g., radioisotope, fluorescent substance) to the RNA as a substrate facilitates detection of a degradation product following electrophoresis.

The polypeptides of the present invention include a polypeptide represented by an amino acid sequence in which one or more amino acid residue(s) is(are) deleted, added, inserted or substituted in the amino acid sequence of SEQ ID NO:1 as long as the polypeptide exhibits an endoribonuclease activity to hydrolyze single-stranded RNA in a sequence-specific manner. Examples of such mutant polypeptides include a polypeptide having 50% or more, preferably 70% or more, more preferably 90% or more homology to the polypeptide of SEQ ID NO:1. Such a mutant polypeptide is encompassed by the present invention even if it recognizes and cleaves a sequence different from the sequence recognized and cleaved by the polypeptide represented by the amino acid sequence of SEQ ID NO:1.

The polypeptide may have a peptide region that is not indispensable to the activity. For example, a polypeptide having the following being attached is included in the polypeptides of the present invention as long as the polypeptide exhibits a single-stranded RNA-specific RNA cleavage activity: a peptide for increasing translation efficiency; a peptide for facilitating purification of the polypeptide (e.g., histidine tag, glutathione-S-transferase, maltose binding protein); or a protein for increasing expression efficiency (e.g., chaperon).

2. The Nucleic Acid Encoding the Polypeptide of the Present Invention

The present invention provides a nucleic acid encoding a polypeptide having a sequence-specific endoribonuclease activity. Such nucleic acids include, but are not limited to, a nucleic acid encoding a polypeptide having a sequence-specific endoribonuclease activity, which is represented by the amino acid sequence of SEQ ID NO:1 or an amino acid sequence in which one or more, for example one to ten amino acid residue(s) is(are) deleted, added, inserted or substituted in said sequence. Examples of amino acid sequences in which one or more amino acid residue(s) is(are) deleted, added, inserted or substituted in the amino acid sequence of SEQ ID NO:1 include an amino acid sequence having 50% or more, preferably 70% or more, more preferably 90% or more homology to the polypeptide of SEQ ID NO:1.

Furthermore, the nucleic acids of the present invention include a nucleic acid encoding a polypeptide having a sequence-specific endoribonuclease activity that is capable of hybridizing to such a nucleic acid under stringent conditions.

The stringent conditions are exemplified by those described in J. Sambrook et al. (eds.), Molecular Cloning: A Laboratory Manual 2nd ed., 1989, Cold Spring Harbor Laboratory. Specifically, under exemplary conditions, incubation with a probe is conducted in 6×SSC containing 0.5% SDS, 5×Denhardt's solution, and 0.01% denatured salmon sperm DNA at 65° C. for 12 to 20 hours. For example, a nucleic acid hybridized with a probe can be detected after removing nonspecifically bound probes by washing in 0.1×SSC containing 0.5% SDS at 37° C.

For example, the nucleic acid encoding the polypeptide of the present invention can be obtained as follows.

A gene having a homology, in terms of the amino acid sequence, to a toxin having an endoribonuclease activity to recognize a specific nucleotide sequence and cleave mRNA (e.g., MazF or PemK) is a candidate for a nucleic acid encoding a polypeptide having a sequence-specific ribonuclease activity. For example, such a candidate gene can be found in a bacterial genome. Five toxins of the PemK family are found in Nitrosomonas europaea.

For example, a candidate gene can be isolated from a bacterial genome by PCR using a primer designed based on nucleotide sequence information. If the entire nucleotide sequence is known, the entire sequence of the candidate gene may be synthesized using a DNA synthesizer.

A protein can be expressed from a candidate gene using an appropriate host (e.g., *Escherichia coli*) transformed with an expression vector having the candidate gene being incorporated. Since expression of a sequence-specific ribonuclease which degrades host RNA can be lethal to the host, it is necessary to strictly suppress the expression of the candidate gene before induction. For example, it is preferable to utilize an expression system such as the pET system (Novagen) which utilizes a promoter for T7 polymerase, or the pCold system (Takara Bio) which is a cold shock expression control system. For conveniently purifying an expression product from a candidate gene, it is advantageous to attach, to the expression product, a peptide for facilitating the purification (e.g., a histidine tag). For this purpose, one containing a region encoding such a peptide may be used as an expression vector.

An endoribonuclease activity can be measured according to the above-mentioned method in which a single-stranded RNA is used as a substrate. A cleavage site can be identified by primer extension using a cleaved RNA as a template, a primer complementary to the RNA and a reverse transcriptase. Since the extension reaction terminates at the cleavage site in the primer extension, the cleavage site can be identified by determining the chain length of the extended strand using electrophoresis. The nucleotide sequence specificity may be identified further strictly by chemically synthesizing oligoribonucleotides having arbitrary sequences, allowing the expression product of the candidate gene to act on them, and determining the presence of cleavage using denaturing acrylamide gel electrophoresis or the like.

3. The Method for Producing the Polypeptide of the Present Invention

For example, the polypeptide of the present invention can be produced by (1) purification from a culture of a microorganism producing the polypeptide of the present invention or (2) purification from a culture of a transformant containing a nucleic acid encoding the polypeptide of the present invention.

Examples of the microorganisms producing the polypeptide of the present invention include, but are not limited to, bacteria of the genus *Nitrosomonas*. For example, the polypeptide of the present invention can be obtained from *N. europaea*, preferably *N. europaea* ATCC19718. The microorganism may be cultured under conditions suitable for the growth of the microorganism. The polypeptide of interest produced in the cells or the culture can be purified using a method conventionally used for protein purification such as cell disruption, fractionation by precipitation (e.g., ammonium sulfate orecipitation), various chromatographies (ion exchange chromatography, affinity chromatography, hydrophobic chromatography, molecular sieve chromatography) or a combination thereof.

The polypeptide of the present invention can be obtained from a transformant transformed with a recombinant DNA containing a nucleic acid encoding the polypeptide of the present invention. Preferably, an appropriate promoter is operably linked upstream of a polypeptide-encoding nucleic acid in the recombinant DNA. Since the polypeptide of the present invention may exert a lethal action on a host, it is preferable that the promoter or an expression system including the promoter can strictly control the transcription from the nucleic acid encoding the polypeptide of the present invention. The pET system or the pCold system exemplifies such a system.

The recombinant DNA may be transferred as it is into a cell as a host. Alternatively, it may be transferred being inserted into an appropriate vector (e.g., a plasmid vector, a phage vector or a virus vector). The recombinant DNA may be integrated into the host chromosome. There is no specific limitation concerning the host to be transformed. For example, a host conventionally used in the field of recombinant DNA (e.g., *Escherichia coli, Bacillus subtilis*, yeast, filamentous fungus, plant, animal, plant culture cell, animal culture cell) may be used.

The polypeptide of the present invention produced from such a transformant can be purified utilizing the above-mentioned purification means. If the nucleic acid encoding the polypeptide of the present invention encodes a polypeptide having a peptide for facilitating purification of the polypeptide being attached, the purification is facilitated very much. A high purity polypeptide can be obtained according to a convenient procedure using a purification means corresponding to the attached peptide (e.g., metal chelate resin for histidine tag, glutathione-immobilized resin for glutathione-S-transferase).

4. Degradation of Single-Stranded RNA Using the Polypeptide of the Present Invention An RNA degradation product can be produced by degrading a single-stranded RNA using the polypeptide of the present invention. Since the polypeptide of the present invention can cleave RNA in a nucleotide sequence-specific manner, the average chain length of the generated RNA degradation products is correlated with the occurrence frequency of the nucleotide sequence recognized by the polypeptide. Thus, the present invention provides an RNA degradation product having certain chain length distribution. Furthermore, it is possible to excise a specific region in RNA utilizing the sequence specificity.

Furthermore, it is possible to selectively degrade a single-stranded RNA using the polypeptide of the present invention. In one embodiment of the present invention, it is possible to inhibit protein synthesis by degrading mRNA in a protein synthesis system (e.g., a cell-free translation system or a transformant) using the polypeptide of the present invention. In this case, if mRNA encoding the protein of interest that has been artificially prepared not to contain a nucleotide sequence recognized by the polypeptide of the present invention is placed in the system, only the mRNA escapes from degradation and the protein of interest is specifically produced in the system. This embodiment is particularly useful for production of a highly pure protein.

EXAMPLES

The following Examples illustrate the present invention in more detail, but are not to be construed to limit the scope thereof.

Among the procedures described herein, basic procedures were carried out as described in J. Sambrook et al. (eds.), Molecular Cloning: A Laboratory Manual 3rd ed., 2001, Cold Spring Harbor Laboratory.

Example 1

Isolation of NE1181 from N. Europaea ATCC19718 and Construction of Expression Plasmid An amino acid sequence of a polypeptide encoded in Nitrosomonas europaea ATCC19718-derived NE1181 gene as well as the nucleotide sequence therefor were obtained from NCBI database (accession nos. NP 841237 and NC_004757). A primer NE1181-F (SEQ ID NO:3) and a primer NE1181-R (SEQ ID NO:4) were synthesized for PCR amplification of a DNA region encoding the entire polypeptide based on the information about the nucleotide sequence of NE1181.

Nitrosomonas europaea ATCC19718 genomic DNA was obtained from ATCC (ATCC No. 19718D).

PCR was conducted using Pyrobest DNA polymerase (Takara Bio) as well as 50 ng of the genomic DNA from Nitrosomonas europaea ATCC19718 and the primers NE1181-F and NE1181-R to obtain a 362-bp amplified DNA fragment. The amplified fragment was digested with restriction enzymes NdeI and XhoI and subjected to agarose gel electrophoresis, and a 341-bp DNA fragment was recovered from the gel. A recombinant plasmid was obtained by ligating the 341-bp DNA fragment to a vector pET21a (Novagen) which had been digested with restriction enzymes NdeI and XhoI. This recombinant plasmid was used to transform Escherichia coli JM109. A plasmid was prepared from a colony of a transformant obtained as described above and the nucleotide sequence was confirmed. Then, the plasmid was designated as an expression vector pET-NE1181.

The nucleotide sequence encoding the Nitrosomonas europaea ATCC19718-derived NE1181 polypeptide inserted in the expression vector pET-NE1181 and the amino acid sequence of the polypeptide are shown in SEQ ID NOS:2 and 1, respectively. In the polypeptide expressed using the expression vector pET-NE1181, a histidine tag that consists of eight amino acid residues including six histidine residues is attached at the C terminus of the polypeptide of the amino acid sequence of SEQ ID NO:1.

Example 2

Preparation of N. europaea ATCC19718-derived NE1181 polypeptide

The expression vector pET-NE1181 obtained in Example 1 was used to transform Escherichia coli BL21 (DE3) (Novagen) to obtain Escherichia coli for expression, pET-NE1181/BL1 (DE3). The Escherichia coli cell was cultured in 5 ml of LB medium containing 100 µg/ml of ampicillin at 37° C. When OD600 nm reached 0.6, IPTG (Takara Bio) was added at a final concentration of 1 mM to induce expression of the polypeptide. The cultivation was terminated two hours after the initiation of induction, and the cells were collected by centrifugation. The cells were suspended in 300 µl of a lysis buffer (50 mM $NaH_2PO_4$, 300 mM NaCl, 10 mM imidazole, pH 8.0), and disrupted using a sonicator (Handy sonic, Tomy). 20 µl of Ni-NTA agarose (Qiagen) was added to a supernatant collected by centrifugation, and the mixture was allowed to stand at 4° C. for 30 minutes. A precipitate collected by centrifugation was washed twice with 100 µl of a washing buffer (50 mM $NaH_2PO_4$, 300 mM NaCl, 20 mM imidazole, pH 8.0). After washing, the precipitate was suspended in 20 µl of an elution buffer (50 mM $NaH_2PO_4$, 300 mM NaCl, 250 mM imidazole, pH 8.0). A supernatant was collected by centrifugation. The same elution procedure was repeated two more times. A total of 60 µl of a sample containing the NE1181 polypeptide was obtained. A portion of the sample was subjected to SDS-PAGE to confirm that the sample contained a polypeptide of the expected size. The concentration of the NE1181 protein in the sample was about 25 ng/µl.

Example 3

Identification of Nucleotide Sequence Specificity of NE1181 Polypeptide Using Oligoribonucleotides as Substrates Oligoribonucleotides were synthesized and cleavage assays were carried out in order to study the nucleotide sequence specificity of ribonuclease activity of the NE1181 polypeptide obtained in Example 2.

Ten oligoribonucleotides of SEQ ID NOS:5-14 were synthesized as substrates. A 5-µl reaction mixture consisting of 10 µM of one of the oligoribonucleotides, ng/µl of the NE1181 polypeptide obtained in Example 2 and mM Tris-HCl (pH 7.5) was incubated at 37° C. for 30 minutes. The reaction product was subjected to electrophoresis on 20% denaturing acrylamide gel (20% acrylamide, 7 M urea, 0.5× TBE buffer). After staining with SYBR GREEN II (Takara Bio), the fluorescence image was analyzed using a fluorescence image analyzer FMBIO II Multiview (Takara Bio). Cleavage modes of the respective oligoribonucleotides are shown in Table 1.

The cleavage modes are indicated as follows: +++: complete cleavage; ++: partial cleavage; +: very little cleavage; and −: complete lack of degradation. Furthermore, the sequence specificity was estimated by comparison of nucleotide sequences surrounding the cleavage sites in view of the presence or the degree of cleavage of each oligoribonucleotide. The results are shown in Table 2.

Based on the results, it was shown that the NE1181 polypeptide preferentially recognizes a sequence 5'-GA/AU-3', 5'-G/AAU-3', 5'-AA/AU-3 or 5'-A/AAU-3' (/represents the cleavage site) to cleave RNA. It was shown that the NE1181 polypeptide is an endoribonuclease having nucleotide sequence specificity quite different from that of MazF,

TABLE 1

| Name | Nucleotide sequence and cleavage site (/ represents cleavage site) | Cleavage NE1181 | SEQ ID NO: |
|---|---|---|---|
| mazG18_12 | AGAAGGAGAUAUACAUAUG / AAUGA / AAUCGG | +++ | 5 |
| MRI011 | AAAGA A / AUCUGA AGUCUGA / AUUCUA | +++ | 6 |
| ABC005 | CAGGAGUCUCAAUCCAGGUUU | – | 7 |
| MRI020 | GGGCUAAUCCAAACUCUUUACCCGUCCUG | – | 8 |
| MRI026 | AUGUACAGGGAUGUCCUAUGUACUAUGGGG | – | 9 |
| MRI028 | UUCACAUAGGGUAUGCAUAUGGAGACAUAG | – | 10 |
| ABC018 | AUACUGCAGCUACGACUCCUU | – | 11 |
| MRI024 | AUUUACAGGGAUUUCCUAUUUACUAUGGGG | – | 12 |
| MRI013 | GGAAAACUCUCAACUCUUAACUCGG | – | 13 |
| ABC019 | GGUUAUGUACAGGAACGCAUU | – | 14 |

Indication of cleavage: +++: complete cleavage; ++: partial cleavage; +: very little cleavage.

TABLE 2

| Name | Nucleotide sequence | Degree of cleavage NE1181 |
|---|---|---|
| mazG18_12 (1) | G/A A U | +++ |
| mazG18_12 (2) | A/A A U | +++ |
| MRI011 (1) | A A/A U | +++ |
| MRI011 (2) | G A/A U | +++ |
| ABC005 (1) | C A A U | – |
| MRI020 | U A A U | – |
| MRI026 | G G A U | – |
| MRI028 (1) | G U A U | – |
| MRI028 (2) | G C A U | – |
| ABC005 (2) | G A G U | – |
| ABC018 | G A C U | – |
| MRI024 | G A U U | – |
| MRI011 (3) | G A A G | – |
| MRI013 | G A A A | – |
| ABC019 | G A A C | – |

Cleavage site: / represents cleavage site.

INDUSTRIAL APPLICABILITY

The present invention provides a novel sequence-specific endoribonuclease. Since the enzyme can recognize and cleave a specific sequence in RNA, it is useful for analysis of RNA molecules, preparation of RNA fragments, control of cells (e.g., inhibition of protein synthesis) through cleavage of intracellular RNA, and the like.

Sequence Listing Free Text

SEQ ID NO:3; PCR primer NE1181-F to amplify a DNA fragment encoding NE1181 protein.
SEQ ID NO:4; PCR primer NE1181-R to amplify a DNA fragment encoding NE1181 protein.
SEQ ID NO:5; Oligoribonucleotide mazG18_12.
SEQ ID NO:6; Oligoribonucleotide MRI011,
SEQ ID NO:7; Oligoribonucleotide ABC005.
SEQ ID NO:8; Oligoribonucleotide MRI020,
SEQ ID NO:9; Oligoribonucleotide MRI026.
SEQ ID NO:10; Oligoribonucleotide MRI028.
SEQ ID NO:11; Oligoribonucleotide ABC018.
SEQ ID NO:12; Oligoribonucleotide MRI024.
SEQ ID NO:13; Oligoribonucleotide MRI013.
SEQ ID NO:14; Oligoribonucleotide ABC019.

The invention claimed is:

1. A method for degrading a single-stranded RNA, the method comprising allowing a polypeptide having a sequence-specific endoribonuclease activity to act on a single-stranded RNA and to hydrolyze a phosphodiester bond 5' or 3' to the second A residue in the sequence 5'-GAAU-3' or 5'-AAAU-3 in said RNA, wherein said polypeptide is (a) a polypeptide comprising the amino acid sequence of SEQ ID NO:1 or (b) a polypeptide comprising a mutant amino acid sequence which differs from SEQ ID NO:1, said mutant amino acid sequence having 90% or more homology to the amino acid sequence of SEQ ID NO:1.

2. The method according to claim 1, wherein said single-strand RNA is mRNA in a protein synthesis system.

3. The method according to claim 1, wherein the polypeptide of (b) comprises a mutant amino acid sequence that differs from SEQ ID NO:1 solely by one or more amino acid substitutions.

4. The method according to claim 1, wherein the polypeptide of (b) comprises a mutant amino acid sequence that differs from SEQ ID NO:1 solely by a single amino acid deletion, insertion or substitution.

5. The method according to claim 1, wherein the polypeptide of (b) comprises a mutant amino acid sequence that differs from SEQ ID NO:1 solely by a single amino acid substitution.

6. The method according to claim 1, wherein the polypeptide is the polypeptide of (a).

7. The method according to claim 1, wherein the polypeptide consists of SEQ ID NO:1.

* * * * *

SEQUENCE LISTING

<160> NUMBER OF SEQ ID NOS: 14

<210> SEQ ID NO 1
<211> LENGTH: 113
<212> TYPE: PRT
<213> ORGANISM: Nitrosomonas europaea ATCC 19718

<400> SEQUENCE: 1

```
Met Thr Asp Phe Lys Gln Arg Asp Ile Tyr Trp Ile Asp Leu Glu
 1               5                  10                  15

Pro Thr Lys Gly Ala Glu Thr Arg Lys Leu Arg Pro Cys Val Ile
               20                  25                  30

Ile Gln Ser Asp Leu Val Asn Val Gln Ser Arg Thr Val Ile Val
               35                  40                  45

Ala Pro Leu Leu Leu Gln His Lys Pro Trp Pro Phe Ala Val Asn
               50                  55                  60

Leu Glu Pro Thr Glu Lys Asn Gly Leu Asp Lys Asp Arg His Ile
               65                  70                  75

Asn Leu Lys Gln Leu Arg Ala Val Asp Ile Ser Arg Ile Gly Lys
               80                  85                  90

Lys Gln Gly Arg Leu Glu Asn Arg Tyr Lys Asp Pro Ile Lys Ala
               95                 100                 105

Ala Leu Met Ile Ile Phe Asp Leu
              110

<210> SEQ ID NO 2
<211> LENGTH: 339
<212> TYPE: DNA
<213> ORGANISM: Nitrosomonas europaea ATCC 19718

<400> SEQUENCE: 2
atgactgatt tcaagcagcg ggatatttac tggatcgatc ttgaaccgac aaagggtgcg      60
gaaacaagaa aattaaggcc atgtgtaatt attcaaagtg acctggttaa cgttcaatcc     120
agaacagtga tagttgcccc tttgctcctt cagcataaac cctggccatt tgcagtgaat     180
ctggagccca cagaaaaaaa tggtctggat aaggatcgtc atatcaacct caagcaatta     240
cgcgcggttg atatttcacg cattggaaaa aaacaaggca ggcttgaaaa tagatacaag     300
gatcctatca aagcagcttt aatgatcatc tttgatttg                           339

<210> SEQ ID NO 3
<211> LENGTH: 33
<212> TYPE: DNA
<213> ORGANISM: Artificial
<220> FEATURE:
<223> OTHER INFORMATION: PCR primer NE1181-F to amplify a DNA fragment
      encoding NE1181 protein.

<400> SEQUENCE: 3
ggggagctaa catatgactg atttcaagca gcg                                   33

<210> SEQ ID NO 4
<211> LENGTH: 36
<212> TYPE: DNA
<213> ORGANISM: Artificial
<220> FEATURE:
<223> OTHER INFORMATION: PCR primer NE1181-R to amplify a DNA fragment
      encoding NE1181 protein.

<400> SEQUENCE: 4
ggggctcgag caaatcaaag atgatcatta aagctg                                36

<210> SEQ ID NO 5
<211> LENGTH: 30
<212> TYPE: RNA
<213> ORGANISM: Artificial
<220> FEATURE:
<223> OTHER INFORMATION: Oligoribonucleotide mazG18_12.

<400> SEQUENCE: 5
```

-continued agaaggagau auacauauga augaaaucgg                                            30

<210> SEQ ID NO 6
<211> LENGTH: 25
<212> TYPE: RNA
<213> ORGANISM: Artificial
<220> FEATURE:
<223> OTHER INFORMATION: Oligoribonucleotide MRI011.

<400> SEQUENCE: 6
aaagaaaucu gaagucugaa uucua                                                 25

<210> SEQ ID NO 7
<211> LENGTH: 21
<212> TYPE: RNA
<213> ORGANISM: Artificial
<220> FEATURE:
<223> OTHER INFORMATION: Oligoribonucleotide ABC005.

<400> SEQUENCE: 7
caggagucuc aauccagguu u                                                     21

<210> SEQ ID NO 8
<211> LENGTH: 29
<212> TYPE: RNA
<213> ORGANISM: Artificial
<220> FEATURE:
<223> OTHER INFORMATION: Oligoribonucleotide MRI020.

<400> SEQUENCE: 8
gggcuaaucc aaacucuuua cccguccug                                             29

<210> SEQ ID NO 9
<211> LENGTH: 30
<212> TYPE: RNA
<213> ORGANISM: Artificial
<220> FEATURE:
<223> OTHER INFORMATION: Oligoribonucleotide MRI026.

<400> SEQUENCE: 9
auguacaggg auguccuaug uacuaugggg                                            30

<210> SEQ ID NO 10
<211> LENGTH: 30
<212> TYPE: RNA
<213> ORGANISM: Artificial
<220> FEATURE:
<223> OTHER INFORMATION: Oligoribonucleotide MRI028.

<400> SEQUENCE: 10
uucacauagg guaugcauau ggagacauag                                            30

<210> SEQ ID NO 11
<211> LENGTH: 21
<212> TYPE: RNA
<213> ORGANISM: Artificial
<220> FEATURE:
<223> OTHER INFORMATION: Oligoribonucleotide ABC018.

<400> SEQUENCE: 11
auacugcagc uacgacuccu u                                                     21

<210> SEQ ID NO 12
<211> LENGTH: 30
<212> TYPE: RNA
<213> ORGANISM: Artificial
<220> FEATURE:

```
<223> OTHER INFORMATION: Oligoribonucleotide MRI024.

<400> SEQUENCE: 12
auuuacaggg auuuccuauu uacuaugggg                          30

<210> SEQ ID NO 13
<211> LENGTH: 25
<212> TYPE: RNA
<213> ORGANISM: Artificial
<220> FEATURE:
<223> OTHER INFORMATION: Oligoribonucleotide MRI013.

<400> SEQUENCE: 13
ggaaaacucu caacucuuaa cucgg                               25

<210> SEQ ID NO 14
<211> LENGTH: 21
<212> TYPE: RNA
<213> ORGANISM: Artificial
<220> FEATURE:
<223> OTHER INFORMATION: Oligoribonucleotide ABC019.

<400> SEQUENCE: 14
gguuauguac aggaacgcau u                                   21
```